United States Patent [19]

Smyth

[11] Patent Number: 5,162,267

[45] Date of Patent: Nov. 10, 1992

[54] RADIO-OPAQUE CALCIUM PHOSPHATE GLASS

[76] Inventor: Milagros B. Smyth, 7 Wood Cir., East Brunswick, N.J. 08816

[21] Appl. No.: 766,783

[22] Filed: Sep. 27, 1991

[51] Int. Cl.$^5$ ............................................... C03C 3/16
[52] U.S. Cl. ........................................ 501/45; 106/35
[58] Field of Search ................. 501/1, 45, 10; 106/35

[56] References Cited

U.S. PATENT DOCUMENTS 4,604,097  8/1986  Graves, Jr. et al. ................... 623/11

*Primary Examiner*—William R. Dixon, Jr.
*Assistant Examiner*—Chris Gallo
*Attorney, Agent, or Firm*—Samsom B. Leavitt; Michael A. Leavitt

[57] ABSTRACT

A biocompatible, strong, radio-opaque high melting glass is obtained by reacting at the melt mono-basic calcium phosphate with phosphoric acid and a radio-opaque-imparting component such as bismuth oxide ($Bi_2O_3$) or barium oxide (BaO). After soaking, cooling and drying, the glass may be ground to desired particle size, and is admirably suited for use as a filler, binder, or structural mass in the dental and medical fields.

20 Claims, No Drawings

RADIO-OPAQUE CALCIUM PHOSPHATE GLASS

This invention relates to a new calcium phosphate glass material which is bio-compatible, very strong and exhibits radio-opacity enhancing its utility in the dental and medical fields.

BACKGROUND OF THE INVENTION

In the ever-expanding field of bio-engineering and especially in the medico-engineering field, the provision of biocomcompatible, high-strength, conveniently fabricated and formulated products for implants and/or bone replacements is a constantly sought and demanding desideratum. Hydroxyapatite ($Ca_5(PO_4)_3OH$) which is the normal and inorganic structural basis of bone has been widely studied and used in the medical and dental fields, and this material is, then, obviously approved by the United States Food and Drug Administration for use in human beings.

All of the apatitic materials, as well as related calcium phosphates presently in use are crystalline materials requiring very high temperatures (e.g. 1400°–1600° C.) with concomitant high degrees of shrinkage (25–50%) in their fabrication into implants and the like.

The use of the highly refractory apatitic compounds and other bio-acceptable calcium phosphates has not been the panacea for the purposes described above since they do not solve the obvious difficulties inherent in the handling of such infusible substances.

Many of the phosphatic compounds also undergo decomposition at the high temperatures found necessary in the fabrication of shaped structures. As described in U.S. Pat. No. 4,135,935 one solution has been to provide a highly siliceous glass matrix for the refractory material (e.g. fluorapatite) and form a shaped body by compressing and molding a comminuted mixture of the finely ground glass and the fluorapatite under very high pressure and then sintering the mass at about 670° C. (1238° F.). The glass may contain a radio-active compound, e.g. thorium oxide ($ThO_2$) or a ray-absorbing compound such as lead oxide (PbO).

In a related area it is known to provide radiation shielding glass, and specifically, even a phosphate glass. Thus, in U.S. Pat. No. 3,149,234 there is described a low melting, (<350° C.) soft phosphate glass with high amounts of lead, mercury, and/or tantalum. This patent, while mentioning the use of bismuth trioxide and even exemplifying same in but one of twenty-five examples, (and in this example only very small amounts are shown), there is patently no contemplation or suggestion of bio-engineering use; no teaching of a calcium phosphate material, and no provision of a strong, high melting, but workable, glass. U.S. Pat. No. 2,518,194 also discloses an X-ray shielding phosphate glass with high lead and tungsten content. The use of calcium oxide (CaO) is mentioned just once, and, briefly (Col. 3 line 33). but nowhere is it shown as a component in any glass batch.

Some other prior art of interest relates to phosphate ceramic bodies, generally useful as electrical insulating materials In this regard, attention is directed to U.S. Pat. No. 2,486,812 describing a glassy metaphosphate binder for a ceramic body. Generally, the glass matter is comprised of from 85% to 95% by weight of an iron or aluminum phosphate fused with a minor (3 to 15%) amount of fluorspar.

In a similar vein to the foregoing, we also find of interest ceramic glazes and linings. Here we find, illustratively, U.S. Pat. No. 1,654,404 (a phosphatitic material) and U.S. Pat. Nos. 2,204,582, 3,035,937, and 4,481,036, none of which, however are phosphate-containing.

SUMMARY OF THE INVENTION

A bio-compatible, high strength, low shrinkage calcium phosphate glass which is fusible at much lower temperatures (fusible at about 1000° C.) than previously employed crystalline calcium phosphates (fusibility range about 1400° C. to about 1600° C.) is provided by a process which involves heating a mixture containing mono-basic calcium phosphate of the formula [$CaH_4(PO_4)_2 * H_2O$], a different phosphorus compound and a heavy metal compound at elevated temperatures, generally from about 1600° F. to about 2000° F., and then isolating the fusible mass reaction product. Minor quantities of fluoride sources, as well as magnesium compounds, among others may desirably, and in the case of fluoride compounds preferably, be used in the mix for processing in accordance herewith. The inventive glass products are also moisture resistant, useful in fiber optics.

DETAILED DESCRIPTION OF THE INVENTION

The major component used in the process for preparing the unique glassy phosphate of this invention is monobasic calcium phosphate. This product has a Ca/P ratio (on an atoms basis) of 1:2 and a $CaO/P_2O_5$ ratio of 1:1. Hydroxyapatite on the other hand has a Ca/P ratio (on a similar basis) of 1.67:1 and a $CaO/P_2O_5$ ratio of 10:3.

The second essential component used in the processing mixture is a phosphorus-containing compound, and generally, a phosphorus-containing acid. A preferred acid is ortho-phosphoric acid.

A third, and generally preferred (especially for biomedical applications) component of the glass-forming mixture is a metal compound, particularly one which imparts radio-opacity to the glass. Of particular usefulness are bismuth oxide ($Bi_2O_3$) and barium oxide (BaO), with bismuth being the most preferred metal.

The amounts of the aforementiond three components of the mix may be expressed in terms of the molar ratios of the monobasic calcium phosphate (I), the phosphorus (II) from the phosphorus-supplying compound, and the heavy metal (III). Useful ranges for these components based on 100 moles of I, are about 20 to 500 moles of II, and 1 to 50 moles of heavy metal III. A preferred range for each 100 moles of I is 35 to 200 moles of II, and 2 to 40 moles of III. A more preferred range for each 100 moles of I is 50 to 150 moles of II, and 5 to 30 moles of III. Illustrative ratios based on component I, ortho-phosphoric acid (as component II), and bismuth trioxide as component III are as follows:

(A)
10 moles of I
7.5 moles of II
1.0 mole of III
(B)
10 moles of I
10 moles of II
1.5 moles of III
(C)
10 moles of I 7.5 moles of II
1.0 mole of III
0.5 moles of Barium oxide (IIIA)

(D)
10 moles of I
10 moles of II
2.0 moles of IIIA

As described earlier, minor amounts of other adjuvants particularly fluorine-providing compounds as well as other metal compounds may be advantageous. Such adjuvants may be used in amounts to supply from about 0.1 weight % to about 20 weight % of non-heavy metal compounds, elemental fluorine and the like. It is preferred, in most instances, to use no more than about 6,7, 10 or 15 wt. % of the adjuvant with the generally preferred range being from about 0.5 wt. % to about 10 wt. %. in the case of fluorine, A highly preferred range is about 0.5 wt. % to about 2.5 wt. % of elemental fluorine. Similar amounts for generally preferred, and highly preferred use also obtain with low molecular weight metals such as magnesium, iron, and the like. Examples of suitable fluorine compounds are alkali metal and alkaline earth metal fluorides such as sodium fluoride, potassium fluoride, lithium fluoride, calcium fluoride, magnesium fluoride, sodium monofluorophosphate, and the like. As a source of low molecular weight metals, mention may be made of magnesium oxide, magnesium hydroxide, and the like.

The preferred phosphoric acid is usually the 85% acid (liquid) of commerce and industry. The other compounds utilized in this invention are generally available in granular or fine powder form. It is advantageous to prepare the mix which is to be processed from an intimate mixture of the powders and acid.

Where radio-opacity is not necessary or desired, the heavy metal may be omitted. An example of such usage is in the field of fiber optics.

The general process for treating the mixture of reactants is to place them in a suitable reaction vessel to withstand the high temperatures used. As a suitable vessel one may use a high alumina receptacle (e.g. crucible). The reaction mixture is placed in a furnace e.g. an electric or gas-fired furnace and heated to the selected reaction temperature, which is preferably about 1600° F. to 2000° F. and generally in the area of about 1800° F. Depending on the batch size and furnace characteristics and mode of use, it will generally take up to several hours to reach the selected reaction temperature. The reaction mass begins to form a fused, glassy product, and it is then held ("Soaked") at the reaction temperature (also "Fusion" temperature) for minutes to hours, e.g. 30 minutes to 2 to 3 to 4 hours. The main factors dictating the soaking time are the specifically chosen ingredients and the amounts thereof used. After soaking, the glass-like reaction product may be readily molded while still hot, and in a fused and molten stateinto any desired shape dictated by the specific intended use. Thus, the material may be spun or extruded into fibers or films or the like, or molded by any known technique conventional in the molding art. Alternatively, the molten reaction mass may be quenched (e.g. in cold water) as an initial step in producing a granular or powder form of the glass. The powder may serve as a glass matrix or as a filler with and for other substances. In the dental area, the powdered glass in suitable particle size (e.g.-0.1 to 10 microns) is an admirable filler for dental composites (e.g. those based on BIS-GMA), pit and fissure sealants, dental adhesives for crowns, orthodontic brackets, etc. The particulate reaction product may be molded with or without additives for innumerable bio-medical applications.

The process of this invention, as earlier stated, converts the crystalline, non-fusible monobasic calcium phosphate to a glassy phosphate. This conversion is accompanied by a significant change in the CaO and $P_2O_5$ content of the reaction products In the initial compound I, the phosphorus content, expressed as $P_2O_5$, is 56.3% by weight, and the calcium content, expressed as CaO is 22 2% by weight. In the final glassy product, the phosphorous content (as $P_2O_5$) is increased by at least about 10% (i.e. to >62%) as compared to 56.3% in the starting monobasic calcium phosphate, and the calcium content as (CaO) decreased by at least 5% (i.e. to about 21%) and as much as about 35% (i.e. to about 15%). Where heavy metals and/or fluoride are used, there is, of course, a concomitant and substantially equivalent content of fluorine and metal oxide. Significantly, even where only Compounds I and II are used in the process (i.e. no fluorine, heavy metal or other adjuvants are present), there is usually a decrease in the calcium content.

Generally, $P_2O_5$ contents may range from about 62 wt. % to about 90 wt. %; CaO content from about 16 wt. % to about 30 wt. %, heavy metal oxide (e.g. $Bi_2O_3$) from about 1 to 15 wt. %.

For bio-medical applications, $P_2O_5$ values may range from 62 wt. % to about 80 wt. %, and preferably from about 65 wt. % to about 75 wt. %.. In these products the CaO values may range from about 15 wt. % to about 20 wt. %, and preferably from about 16 wt. % to about 18.5 wt. %, with the balance comprising such adjuvants as heavy metal oxide (e.g. 1–10%), fluorine(0-.5–5%), etc.

For fiber optic uses (desirably, no fluorine or heavy metal) the $P_2O_5$ values may range from about 70 wt. % to about 90 wt. %, and preferably from about 72 wt. % to about 88 wt. %, and more preferably from about 75 to 85 weight %, and the CaO content may range from about 10% to about 30% by weight, preferably from about 12% to about 28% by weight, and more preferably from about 15% to about 25% by weight.

The following examples will serve to illustrate the present invention without being deemed limitative thereof. As employed herein and in the appended claims, amounts and proportions are by weight and temperatures are in °F. unless otherwise indicated.

EXAMPLE I

A mixture is prepared from the following ingredients:

| AMOUNT | MOLES | INGREDIENT |
|---|---|---|
| 1000 gms. | 4.0 | Monobasic calcium phosphate (M.W.-252.17) |
| 434 gms. | 4.4 | Ortho-phosphoric acid (MW-98.04) [supplied as 300 cc. of 85% acid] |
| 100 gms. | 0.2 | Bismuth trioxide ($Bi_2O_3$-M.W.-466) |
| 50 gms. | 1.2 | Sodium fluoride (M.W.-42) |

A uniform mixture of the above ingredients is placed in a high alumina crucible and fired in an electric furnace until the mixture reaches 1900° F. The mass is held at this temperature for 30 minutes and then poured into a bucket of cold water. The resultant glass reaction product is then dried in an oven at 150° F., and thereafter cooled to room temperature. The product is then ground to an average particle size of about 10 microns for use as a dental composite or cement filler. The glass has the following composition:

| | |
|---|---|
| $P_2O_5$ | 70.17% |
| CaO | 17.42% |
| $Na_2O$ | 2.87% |
| $Bi_2O_3$ | 7.78% |
| F | 1.76% |
| | 100.00% |

The glass product can readily be softened below about 1900° F. (below about 1050° C.), and may be formed into filaments, rods, sheets, and other shaped structures by conventional techniques.

EXAMPLE II

The procedure of EXAMPLE I is repeated except that the molten, glassy material, after soaking, is cast into thin (¼") slabs directly from the molten reaction mass, and without going through the quenching step.

EXAMPLE III

Examples I and II are repeated except that only the monobasic calcium phosphate and phosphoric acid are used in the reaction mixture to prepare the glass. The final product is a glassy material adaptable for use in fiber optics. the glass product contains 80.1% $P_2O_5$ and 19.9% CaO.

EXAMPLE IV

The product of EXAMPLE I, without quenching, is formed directly into monofilaments varying in diameters from 1 to 10 mils.

EXAMPLE V

The powdered product of EXAMPLE I is formulated with BisGMA to form a 2-part, paste-paste dental composite-forming composition of the following make-up:

| PART A | |
|---|---|
| PARTS | INGREDIENT |
| 72 | Powder of EXAMPLE I (av. part. size 10μ) |
| 21 | Bis-GMA |
| 6 | Hexanediol Dimethacrylate |
| 1 | Acetyl thiourea reductant |

PART B

Same as PART A but in place of the thiourea reductant, there is used 2 parts of cumene hydroperoxide.

When equal parts of A and B are mixed, curing is initiated by the redox system resulting from the admixture of the 2 parts. The resultant cured composition forms an excellent dental composite of high compressive strength.

EXAMPLE VI

EXAMPLE V is repeated except that the powdered filler of EXAMPLE I is silanated as described in U.S. Pat. No. 3,066,112, the entire disclosure of which is incorporated herein by reference. In this EXAMPLE VI, the silanation is carried out by mixing 0.5% of an aqueous solution of tris(2-methoxyethoxy) vinyl silane catalyzed with sodium hydroxide (to a pH of 9.3–9.8) per unit weight of filler of EXAMPLE I, drying the resultant slurry at 125° C., and then cooling. The resultant composite has excellent compressive strength characteristics.

EXAMPLE VII

A light-curable, dental composite formulation of the following thoroughly mixed ingredients is prepared:

| PARTS | INGREDIENT |
|---|---|
| 75 | Silanated powdered glass filler of EXAMPLE VI |
| 15 | BIS-GMA |
| 4 | hexanediol dimethacrylate |
| 0.4 | N,N-dimethylaminoethylmethacrylate |
| 0.06 | Camphoroquinone |

The foregoing composition when used for a dental composite and cured with high intensity-visible light well-known in the art, yields an excellent, stable, strong, well-bonded composite.

EXAMPLE VIII

The process of EXAMPLE I is repeated using 1000 gms. of monobasic calcium phosphate with the following ingredients and amounts thereof:

A.
289 gms. Phosphoric acid, and
200 gms. Bismuth trioxide

B.
217 gms. Phosphoric acid, and
150 gms. Bismuth trioxide

C.
588 gms. Phosphoric acid (6 moles),
75 gms. Bismuth trioxide, and
100 gms. Barium oxide D.
980 gms. Phosphoric acid,
60 gms. Bismuth trioxide,
40 gms. Calcium fluoride, and
42 gms. Sodium fluoride The examples A, B, C, and D represent glass products which have $P_2O_5$ weight contents of 63.7%, 66.1%, 71.5%, and 77.1% respectively. The mole % ratio of $P_2O_5$/CaO ranges from about 1.28 to about 3 5, and the atoms ratio P/Ca ranges from about 2.5 to 7.0.

EXAMPLE IX

EXAMPLE III is repeated using the following amounts in lieu of the 300 cc. (433.5 grams A.I.-i.e. 100% active) of phosphoric acid used in EXAMPLE III:

A. 50 cc. of phosphoric acid (72.3 gms.)
B. 100 cc. of phosphoric acid (144.6 gms.)
C. 400 cc. of phosphoric acid (578.4 gms.)
D. 1356 cc. of phosphoric acid (1960 gms.A.I.-equivalent to 20 moles of $H_3PO_4$ or 10 moles of $P_2O_5$).

EXAMPLE X 500 grams of the powdered glass product of EXAMPLE I is thoroughly mixed with 500 grams of hydroxyapatite, and is molded in a multi-cavity mold under high pressure (100 atmospheres) and temperature (1600° F.) to produce "blanks" for subsequent shaping (e.g. by grinding, milling, cutting, drilling, etc.) to form teeth and other bone replacements. A suitable attachment means, where indicated, may be provided either integrally from the mix material itself, or by molding the glass matrix-hydroxyapatite composite with a metal or other insert as known in the art.

The powdered mix may also be applied as a coating or glaze on a shaped or preformed substrate (e.g. metal prosthesis).

EXAMPLE XI

To strengthen the glass products of this invention for use for example in load-bearing oral implants, EXAMPLE X is repeated using 600 grams instead of 500 grams of the powdered glass product of EXAMPLE I AND 400 grams of partially stabilized zirconium oxide instead of the 500 grams of hydroxyapatite.

The proportions of the stabilized zirconium oxide in this example may range from about 10 to about 45% by weight of its mixture with the powdered glass product of this invention, and should have a very fine, submicron to micron, particle size. The stabilized zirconium oxide is well known and commercially available from several sources, including Alcoa, GE, IBM and Magnesium Elektron, Inc*. The zirconium oxide is stabilized with from about 3 to about 15% of a number of different metal oxides. For example, Product Data Sheet No. 309 of Magnesium Elektron, Inc. lists as available zirconium oxide stabilized with from 4 to 8% of calcium oxide, magnesium oxide or yttrium oxide and having average particle sizes of 16 to 25 um and specific surface areas of 1.0 to 2.0 $m^2g^{-1}$.

*Flemington, N.J. 08822

The quantities of the ingredients of the products of the present invention may also be expressed in terms of the mole percent of phosphorus pentoxide, calcium oxide, heavy metal oxide, fluorine, sodium oxide ($Na_2O$), etc. In general, the mole % of $P_2O_5$ which may vary from about 48 mole % to about 85 mole %, with a range of 50 to 60 mole % preferred for bio-engineering uses, and about 60 to about 85 mole % preferred for fiber optic applications. The mole % of CaO may range from about 15 to about 52 mole %, with a range of about 25 to 45 mole % preferred for most contemplated uses. Heavy metal (for radio-opacity) and fluorine may range from about 1 mole % to about 25 mole %, with a preferred range of about 1.5 to 15 mole %

The most highly preferred parameters for biomedical and bio-engineering applications are a weight percent of $P_2O_5$ of from about 62 to 72 %, a weight percent of CaO of from about 16.5 to about 19.5 with the other ingredients selected from within the limits given earlier. The weight percent criteria should be used along with the mole % guidelines for optimum results.

Other characteristics of the glass compositions of this invention reside in a ratio of elemental phosphorus atoms to calcium of from about 2.5:1 to about 7.0:1, and a mole % ratio of $P_2O_5$ to CaO of from about 1 25:1 to about 3 5:1.

While this invention has been exemplified with respect to specific processing techniques and conditions, specific ingredients and amounts thereof, and utilities, all variations thereof obvious to one skilled in the art are intended to be included within the spirit and purview of this application and the scope of the appended claims

I claim:

1. A process for preparing a high strength, biocompatible calcium phosphate glass which comprises heating a mixture of monobasic calcium phosphate (I) and phosphoric acid (II) in a $P_2O_5$ molar ratio of I:II ranging from about 11:1 to about 1:3, to a temperature and for a time sufficient to convert the mixture to a glass reaction product.

2. A process as defined in claim 1, wherein the mixture includes a radio-opaque metal source.

3. A process as defined in claim 2 wherein the metal source is bismuth trioxide.

4. A process as defined in claim 2 wherein the metal source is barium oxide.

5. A process as defined in claim 1 wherein the mixture includes a fluorine compound.

6. A process as defined in claim 5 wherein the fluorine compound is sodium fluoride.

7. A process as defined in claim 1 wherein the mixture is heated to a temperature of from about 1500° F. to about 2100° F. and soaked in this range for about 10 minutes to about 4 hours.

8. A process as defined in claim 7 which includes in the mixture a metal compound which imparts radio-opacity to the glass reaction product.

9. A process as defined in claim 8 wherein a fluorine compound is included in the glass-forming mixture.

10. A process as defined in claim 1 wherein the mixture contains from 0 to about 10% by weight of a radio-opaque metal and 0 to about 15% by weight of an inorganic fluoro-compound.

11. A process as defined in claim 1 wherein said I:II $P_2O_5$ molar ratio is from about 5:1 to 1:2.

12. A process as defined in claim 10 wherein said I:II $P_2O_5$ molar ratio is from about 5:1 to 1:2.

13. A process as defined in claim 12 wherein the temperature is about 1800° to 2000° F.

14. A process as defined in claim 13 wherein said I:II $P_2O_5$ molar ratio ranges from about 2:1 to about 1:1.5.

15. A process as defined in claim 14 wherein the mixture contains about 1 to 10% by weight of bismuth trioxide.

16. A process as defined in claim 15 wherein the maintenance (soaking) temperature is for about 15 to 75 minutes.

17. A high strength, biocompatible calcium phosphate glass containing from about 62 to 80 weight percent of $P_2O_5$, from about 16 to 20 weight percent of CaO, and about 1-15 weight percent of radio-opaque barium oxide, or bismuth trioxide; or any mixture thereof.

18. A process comprising mixing the powdered product of claim 10 with about an equal weight of hydroxyapatite.

19. A process comprising mixing the powdered product of claim 10 with stabilized zirconium oxide in a respective weight ratio of about 90:10 to about 55:45.

20. A process according to claim 19 wherein the zirconium oxide is stabilized with about 3% to about 15% of calcium oxide, magnesium oxide or yttrium oxide.

* * * * *